US010082682B2

(12) United States Patent
Liang (10) Patent No.: US 10,082,682 B2
(45) Date of Patent: Sep. 25, 2018

(54) METHODS AND SYSTEMS FOR MEASURING HUMAN FACES FOR FITTING, SELECTING, AND OPTIMIZING EYEGLASSES (71) Applicant: PERFECT VISION TECHNOLOGY (HK) LTD., Tsuen Wan (HK)

(72) Inventor: Junzhong Liang, Fremont, CA (US)

(73) Assignee: PERFECT VISION TECHNOLOGY (HK) LTD., Tsuen Wan (HK)

( * ) Notice: Subject to any disclaimer, the term of this patent is extended or adjusted under 35 U.S.C. 154(b) by 0 days.

(21) Appl. No.: 15/372,684

(22) Filed: Dec. 8, 2016

(65) Prior Publication Data

US 2018/0164610 A1 Jun. 14, 2018

(51) Int. Cl.
A61B 3/10 (2006.01)
G02C 13/00 (2006.01)
A61B 3/11 (2006.01)
A61B 3/00 (2006.01)
H04N 13/02 (2006.01)
G06T 19/20 (2011.01)

(52) U.S. Cl.
CPC .......... *G02C 13/005* (2013.01); *A61B 3/0025* (2013.01); *A61B 3/0041* (2013.01); *A61B 3/0091* (2013.01); *A61B 3/112* (2013.01); *G02C 13/003* (2013.01); *G06T 19/20* (2013.01); *H04N 13/0203* (2013.01)

(58) Field of Classification Search
CPC .. A61B 3/112; A61B 3/10; A61B 3/11; A61B 3/111
USPC ........................................ 351/204, 200, 246
See application file for complete search history.

(56) References Cited

U.S. PATENT DOCUMENTS

| 6,095,650 | A | 8/2000 | Gao et al. |
| 7,221,437 | B1 | 5/2007 | Schaefer |
| 9,395,562 | B1 | 7/2016 | Nguyen et al. |
| 9,628,697 | B2 | 4/2017 | Choukroun |
| 2001/0026351 | A1 | 10/2001 | Gao et al. |
| 2004/0189935 | A1 | 9/2004 | Warden et al. |

(Continued)

OTHER PUBLICATIONS

International Search Report and Written Opinion dated Jul. 27, 2017 for PCT Patent Application No. PCT/US2016/065576.

(Continued)

*Primary Examiner* — Hung Dang
(74) *Attorney, Agent, or Firm* — The Mueller Law Office, P.C.

(57) ABSTRACT

Methods and systems include using a digital camera module for capturing a plurality of digital images of a tested subject at a plurality of perspective views. The tested subject is not required to move their head position or viewing direction during the capturing of images. A motion control module I) rotates the camera module with its optical axis pointing at a rotation center to correct any orientation error in capturing the perspective views, and II) positions the camera module to adjust the rotation center for accommodating different head positions of the tested subject. A computer module processes and stores the plurality of digital images to fit an eyeglass frame to the tested subject or to acquire data for fitting prescription lenses into the eyeglass frame. The computer module can provide an augmented reality of different styles of eyeglasses, and obtain 3D measurements for fitting eyeglass frames.

27 Claims, 5 Drawing Sheets (56) References Cited

U.S. PATENT DOCUMENTS

| | | |
|---|---|---|
| 2008/0084481 A1 | 4/2008 | Lindsay |
| 2009/0051871 A1 | 2/2009 | Warden et al. |
| 2010/0283844 A1 | 11/2010 | Sayag |
| 2011/0063449 A1 | 3/2011 | Lee |
| 2011/0242481 A1 | 10/2011 | Wada |
| 2012/0008090 A1 | 1/2012 | Atheimer et al. |
| 2013/0222684 A1 | 8/2013 | Mueller et al. |
| 2013/0222764 A1 | 8/2013 | Thompson et al. |
| 2015/0015848 A1 | 1/2015 | Haddadi et al. |
| 2016/0166145 A1 | 6/2016 | Choukroun et al. |
| 2016/0202499 A1* | 7/2016 | Farache ............... A61B 3/0025 351/204 |
| 2016/0327811 A1 | 11/2016 | Haddadi et al. |
| 2016/0357032 A1 | 12/2016 | Cabeza-Guillen et al. |
| 2017/0038608 A1 | 2/2017 | Cabeza-Guillen et al. |

OTHER PUBLICATIONS

International Search Report and Written Opinion dated Jul. 27, 2017 for PCT Patent Application No. PCT/US2016/065590.
Office Action dated Dec. 6, 2017 for U.S. Appl. No. 15/372,676.
Notice of Allowance dated Apr. 12, 2018 for U.S. Appl. No. 15/372,676.

\* cited by examiner

METHODS AND SYSTEMS FOR MEASURING HUMAN FACES FOR FITTING, SELECTING, AND OPTIMIZING EYEGLASSES

RELATED APPLICATIONS

This application is related to Liang, U.S. patent application Ser. No. 15/372,676, entitled "Methods and Systems for Measuring Human Faces and Eyeglass Frames" and filed on Dec. 8, 2016 even date herewith, which is hereby incorporated by reference for all purposes.

BACKGROUND OF THE INVENTION

A good pair of eyeglasses for vision correction of human eyes requires seeing well through the lenses. Seeing well through the lenses requires obtaining the best refractive prescription possible, and mounting the lenses into eyeglass frames at the perfect location. Mounting the lenses into eyeglass frames involves measuring pupil distances of left and right eyes with a device such as the Essilor® PD meter, and measuring parameters related to the eyeglass frames for personalized free-form lenses. The parameters include, for example, segment height, vertex distances, and pantoscopic tilts, which are measured using systems like Accufit® Digital Measurement systems from LensCrafters™ or i.Terminal 2® from Zeiss. Fitting of the frames also may include virtually trying-on eyeglass frames using tablet-based software applications that capture videos of patients from different perspective views and allow customers to select styles of eyeglass frames.

The Essilor PD meter provides precise measurements of pupil distances, but cannot get the other measurements like Accufit Digital Measurement systems, iTerminal 2, or tablet-based apps for a virtual try-on of eyeglass frames.

Systems like Accufit Digital Measurement and i.Terminal 2 can provide measurements related to the eyeglass frames for personalized free-form lenses, but these systems have issues in matching the pupil distances measured with Essilor PD meters and cannot provide a virtual try-on like the tablet-based apps.

Tablet-based apps are inexpensive tools for providing virtual try-on capabilities, but cannot provide the same precision and reliability in measuring pupilary distance like Essilor PD meter, and the other parameters relating the eyeglass frames for personalized free-form lenses like Accufit Digital Measurement and i.Terminal 2.

Consequently, although many configurations and methods for vision correction are known in the art, all of them suffer from one or more disadvantages. Thus, there is a need to provide improved methods and systems for measuring human faces for fitting, selecting, and optimizing eyeglasses.

SUMMARY

A system for measuring human faces for eyeglasses includes a digital camera module, a motion control module, and a computer module. The digital camera module is positioned to capture a plurality of digital images of a face of a tested subject. The plurality of digital images comprise a plurality of perspective views including a front view and a side view. The digital camera module includes a camera lens, an image sensor, and control electronics capable of acquiring the plurality of digital images. The motion control module rotates the digital camera module around a head of the tested subject with an optical axis of the digital camera module pointing at a specified position in space, where the rotating corrects any orientation error in capturing the plurality of perspective views. The motion control module also positions the digital camera module to adjust the specified position for accommodating different head positions of the tested subject. The computer module processes and stores the plurality of digital images of the face of the tested subject at the plurality of perspective views. The computer module includes a display, a storage unit, and a processor, and is connected to the digital camera module and the motion control module. The processor of the computer module stores instructions to use the plurality of digital images to fit an eyeglass frame to the tested subject or to acquire data for fitting prescription lenses into the eyeglass frame.

A method of measuring human faces for eyeglasses includes using a digital camera module for capturing a plurality of digital images. The plurality of digital images comprise a plurality of perspective views of a face of a tested subject, including a front view and a side view. The tested subject is not required to move their head position or viewing direction during the capturing of the plurality of digital images. A motion control module is used to move the digital camera module. The moving includes I) rotating the digital camera module around the head of the tested subject with an optical axis of the digital camera module pointing at a rotation center, where the rotating orients the digital camera module for capturing the front view and the side view, and II) positioning the digital camera module to adjust the rotation center for accommodating different head positions of the tested subject. A computer module is used for processing and storing the plurality of digital images. The processing includes: i) determining a pupillary distance, a segment height, a vertex distance, or a pantoscopic tilt, ii) providing an augmented reality of different styles of eyeglass frames, or iii) obtaining 3D measurements of the face for fitting different styles of eyeglass frames to the face of the tested subject. The computer module is connected to the digital camera module as well as the motion control module.

DETAILED DESCRIPTION

Providing consumers with an excellent pair of eyeglasses for vision correction of human eyes involves not only seeing well through the lenses of the eyeglasses, but also looking good with frame styles and fitting the frames firmly on the consumer's face. The present methods and systems address fundamental issues for providing the best eyeglasses possible. In this disclosure, a tested subject for which eyeglasses are being fitted may also be referred to as the patient, consumer or wearer. A person operating the system to perform the eyeglass measurements shall be referred to as a user or operator.

Figure 1:
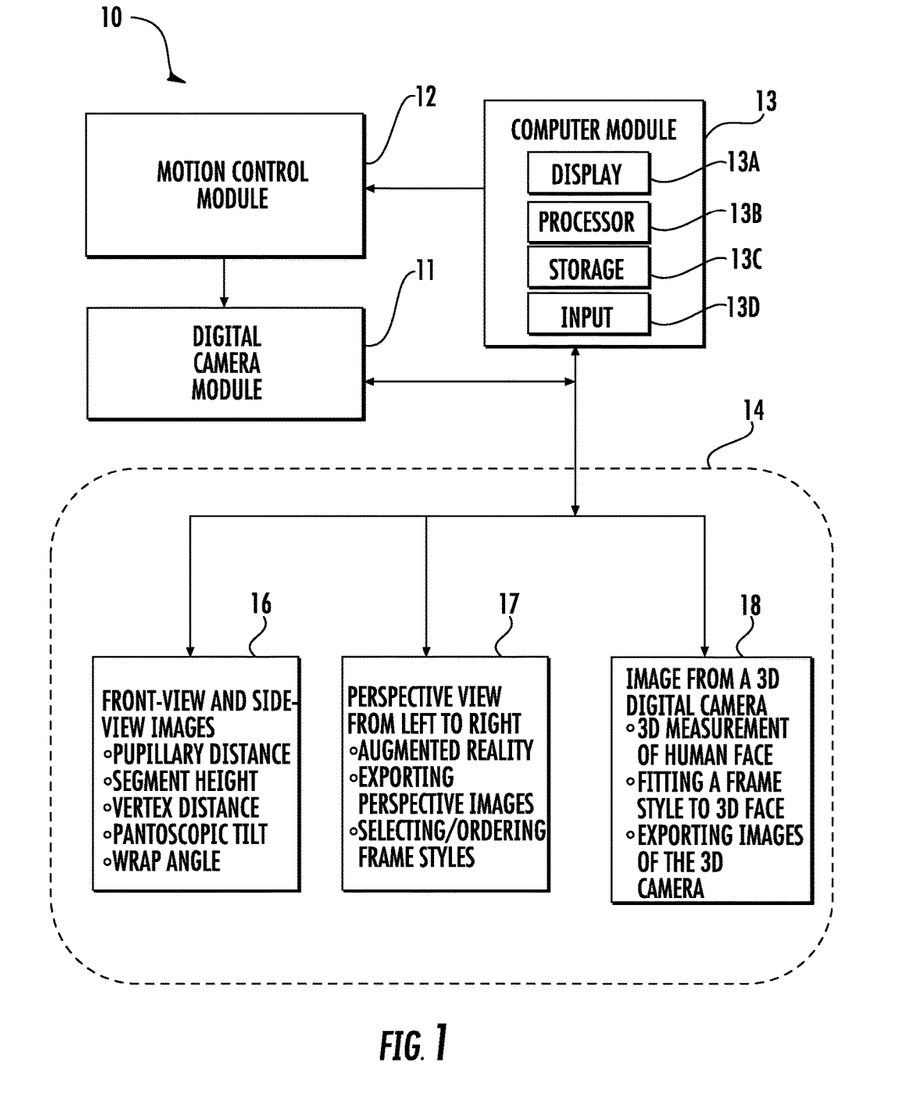
FIG. 1 shows a block diagram of a system for measuring human faces for fitting, selecting, and optimizing eyeglasses in accordance with the present embodiments.

FIG. 1 shows a block diagram of an embodiment of a system 10 for precisely measuring human faces for eyeglass fitting parameters such as pupillary distances, segment height, vertex distance, pantoscopic tilt, and wrap angle, where the measurements are performed in an environment that requires no assistance of the tested subject in response to requests of an operator. Pupillary distance (PD) is the distance from the center of the face to each of the left and right pupils (left PD and right PD). Segment height—also referred to as seg height or SH—is the vertical distance from the bottom of the eyeglass lens to the pupil center of the eye. Vertex distance is the distance between the back surface of the eyeglass lens and the front surface of the cornea. Pantoscopic tilt is the angle that the lower rim of the eyeglass frame is tilted toward the wearer's face. Wrap angle is the horizontal angle that a lens angles toward the face of the wearer, relative to a vertical plane parallel to the face.

The system 10 includes a digital camera module 11 that is positioned to capture digital images of a face of a tested subject. The digital camera module includes a camera lens, an image sensor, and control electronics capable of acquiring images. The control electronics may also be able to save the images. The system 10 also includes a motion control module 12 that moves the camera module around the head while the optical axis of the camera module, which defines the viewing direction, points to a specified location in space. In some embodiments, the digital camera is rotated around a head of the tested subject with the optical axis pointing to a rotation center, which is the specified location. The rotating allows the digital camera module to capture a plurality of perspective views of the face of the tested subject, including a front view and a side view. The rotating corrects any orientation error between the alignment of the camera and the face of the tested subject during capturing the plurality of perspective views. In other words, the ability to rotate the digital camera module enables perfect front views and perfect side views to be captured, while the tested subject by design remains passive and steady without moving his/her head position or viewing direction. The motion control module 12 also is able to position the digital camera module 11 to adjust the rotation center to accommodate different head positions of the tested subject, such as for different heights and postures between test subjects.

A computer module 13 is connected to the digital camera module 11 and to the motion control module 12, and utilizes a software module 14. The computer module 13 in one embodiment includes at least a display 13A, a processor 13B and a storage unit 13C. The storage unit 13C may be, for example, a memory unit within the hardware of the computer module 13 itself, or a memory in another computer server such as cloud-based storage. The computer module 13 is processes and stores the digital images of the face of the tested subject from the digital camera module 11, including a front view, a side view and additional views in the plurality of perspective views.

The processor 13B stores instructions, such as software code, to use the digital images to fit an eyeglass frame to the tested subject and/or to acquire data for fitting prescription lenses into an eyeglass frame properly. For example, the computer module 13 may process the digital images to provide measurements of pupillary distance, seg height, vertex distance, panoramic angle and pantoscopic tilt for fitting prescription lenses into an eyeglass frame. The processor 13B may store instructions to acquire data for fitting prescription lenses into an eyeglass frame properly. The system 10 includes measurement modes to switch between a front view measurement of pupillary distances and seg heights, and a side view measurement of vertex distances and pantoscopic tilts. When switching between the front view and side view measurement modes, the digital camera module 11 will move around the head by using the motion control module 12 instead of requesting the tested subject to turn his/her body around.

The motion control module 12 is controlled by computer module 13 for moving the digital camera module 11. For example, when the tested subject is not directly facing the digital camera module 11, resulting in a misalignment between the patient's face with the camera for a front view or a side view, the digital camera module 11 can be rotated to make the necessary corrections without the need for asking the tested subject to rotate his/her head. The processor 13B provides instructions to the motion control module 12 for the rotating and the positioning of the digital camera module 11 in order to correct an alignment of the front view. The motion control module 12 also moves the rotation center of the camera module linearly (e.g., up-and-down, left-and-right, forward-and-backward) in order to capture an image of the face properly and independently of height difference and head position of the patient. The instructions to move the digital camera module 11 to correct for alignment of the front view and/or adjust for the head position of the tested subject are based on, for example, subjective judgments by an operator through images captured by the digital camera module 11.

In measuring pupillary distances and seg heights, the tested subject is asked to wear an eyeglass frame plus a frame attachment that is decorated with a plurality of calibration marks for determining a calibration factor of digital images. The calibration marks are often designed to define a rectangular region covering the measured eyes with a few marks at each corner. The physical distances in millimeters between the marks are predetermined and known. When images of a face, an eyeglass frame, and a frame attachment are taken, image dimensions in its native unit of pixels can be converted to millimeters once the distance between the marks in the frame attachment is determined in the images captured. The calibration factor may be expressed in, for example, millimeters per pixel. The frame attachment is mountable to the eyeglass frame, and the eyeglass frame is worn by the tested subject during the capturing of the digital images. The digital camera module 11 captures a front view image of the subject with the eyeglass frame and the frame attachment.

The computer module 13 utilizes the software module 14 that performs analysis and calculations used for fitting, selecting, and optimizing eyeglass frames for the patient. The computer code in software module 14 is represented in FIG. 1 as blocks 16, 17 and 18. In block 16, the software module 14 of the computer module 13 processes the image of a front view as follows: 1) identifying the calibration marks on the frame attachment and determining the image scale factors (i.e., calibration factor, such as mm/pixel) for the image captured; 2) identifying pupil centers of the left and right eyes in the captured image, and determining the pupillary distances in number of pixels from pupil center to the center of the face or to the center of the eyeglass frame, and calculating the pupillary distances in mm using the image scale factor (i.e. calibration factor) in mm/pixel; and 3) calculating the distances in millimeters from the pupil centers to frame edges in different directions with the calibration factors and then determining seg height.

In measuring vertex distances and pantoscopic tilts, the tested subject is also required to wear an eyeglass frame plus the frame attachment that is decorated with a plurality of calibration marks for determining calibration factors of digital images in mm/pixels. The digital camera module captures a side view image of the subject with the eyeglass frame plus the frame attachment. The computer module 13 processes of the side view image in block 16 for determining the distance from the lens in the frame to the cornea of the eye as the vertex distance, and determining the angle between the frame to the vertical direction as pantoscopic tilt and wrap angle of the eyeglass frame.

Figure 2:
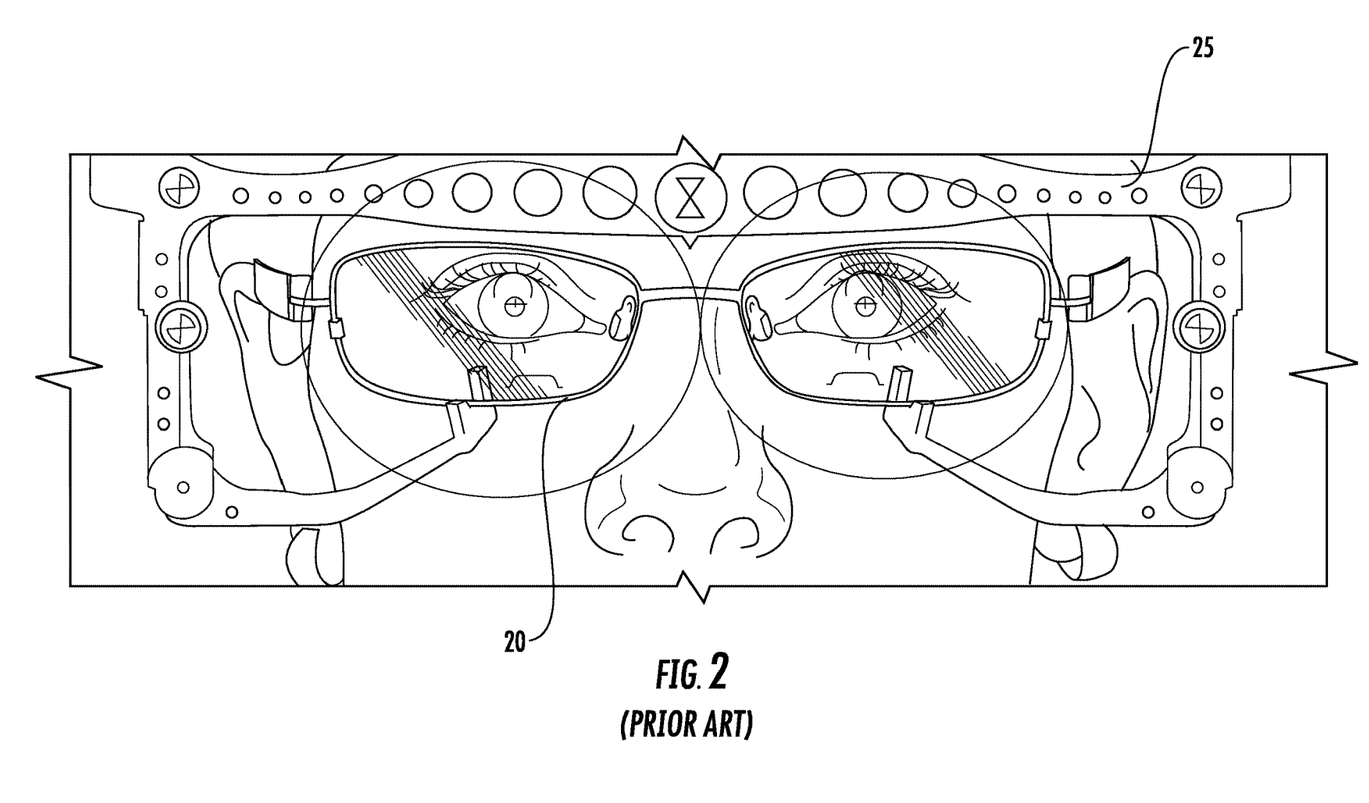
FIG. 2 shows a conventional front view of a human face with an eyeglass frame as known in the art.

The system 10 has a number of advantages compared with conventional systems that have limited adjustment capabilities for digital camera positioning. First, conventional digital camera systems for eyeglass measurements require the use of handheld pupilometers to measure a true pupillary distance. Using a handheld PD meter requires close contact between its operator and the tested subject, which is often uncomfortable to a lot of consumers and operators. Another advantage is that the rotation control of the digital camera module in the present embodiments ensures that the front view is perfectly captured and left and right sides of the eye are absolutely symmetric. This perfect front-view image is a necessary condition for precisely measuring the pupillary distances of the left and right eyes. This ability to adjust rotational position provides improved precision compared to conventional eyeglass measurement systems. This improvement is demonstrated by FIG. 2, which is a typical front view of a human face with an eyeglass frame 20 and frame attachment 25. If the tested face is at an angle from the optical axis of the camera module, the pupillary distance on one side (e.g. left) is over-estimated while the pupillary distance on the other side (e.g. right) is under-estimated. Without the capability of rotating the digital camera around the head, operators using conventional systems must repeatedly ask people to turn their head around in order to get perfect front-view as well as side-view images. This repositioning by the patient is not only difficult and time-consuming, but most likely results in a misalignment.

Figure 3A:
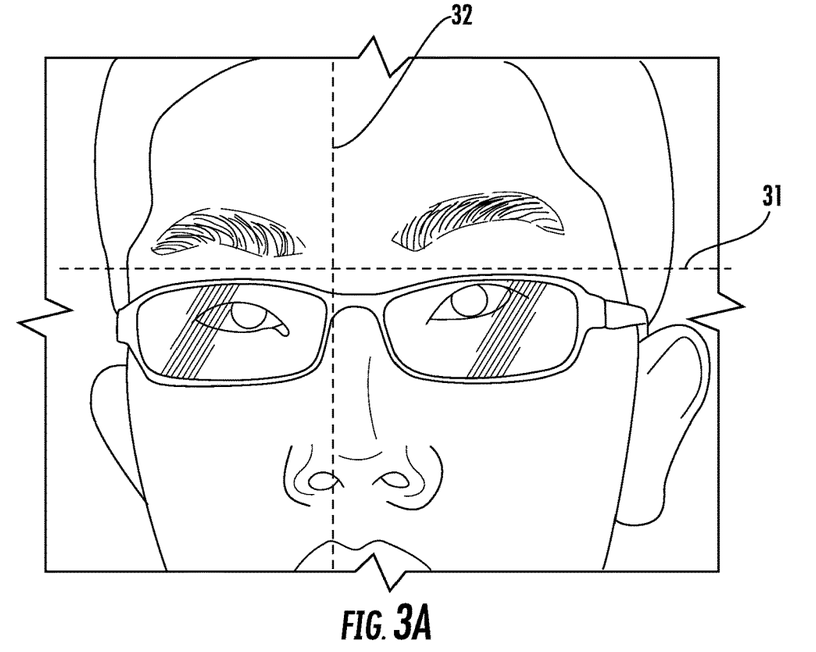
FIG. 3A shows a front view of a human face with an eyeglass frame when the human face is misaligned with the optical axis of the camera system.
Figure 3B:
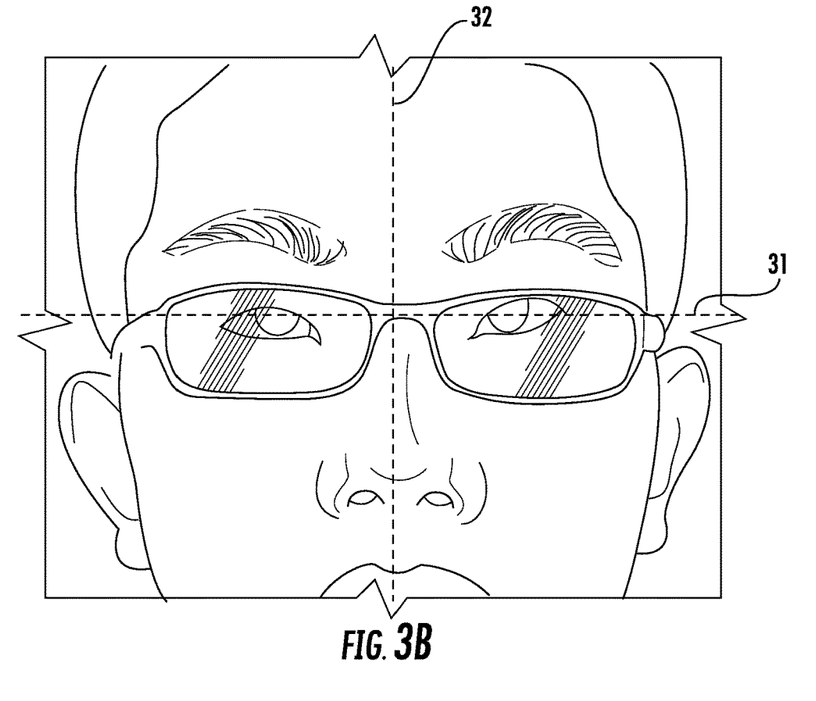
FIG. 3B shows a front view of a human face with an eyeglass frame when the human face is perfectly aligned with the optical axis of the camera system.

The system 10 in the present disclosure can adjust the camera orientation actively without needing any assistance of the tested subject. If the front-view picture is not symmetric as shown by the vertically and horizontally off-center dashed lines in FIG. 3A which represent a horizontal axis 31 and a vertical axis 32 of the camera, an operator can rotate the digital camera module 11 around the head of the patient and produce a symmetric front-view image as shown in FIG. 3B without asking the tested subject to turn their head. This ability to rotate the camera orientation relative to the face of the tested subject can ensure that both the front view and the side view of the eyes are taken at the perfect perspective directions.

In summary, the system in the present embodiments provides one system for all the measurements of pupillary distance, seg height, vertex distance, and pantoscopic tilt. It will also reduce measurement time, and improve precision and reliability of all these measurements. Finally, because the tested subject remains passive and steady without moving his/her head position or viewing direction, the system in the present embodiments is patient-friendly.

Returning to FIG. 1, the system 10 in block 17 has another advantage of capturing a large number of images of the human face at any perspective viewing angle, from one side view to the other side view. This plurality of perspective views from a left side view to a right side view of the face enables an augmented reality of different styles of eyeglass frames for the tested subject by rotating the digital camera module around the head of the tested subject. The captured images can be stored in a database in the computer module, or can also be exported to another computer server and used for post-processing.

Capturing a large number of perspective views of human face with or without an eyeglass frame can be used for augmented reality of different styles of eyeglass frames. This can be achieved by software module 14 in the present systems by retrieving images of different styles of eyeglass frames from a database, and superimposing images of different styles of eyeglass frames onto the plurality of perspective views of the face that have been captured, for displaying an appearance of the subject with a desired frame style. The superimposed images can then be viewed by the patient for selecting and ordering frame styles.

Conventional tablet-based systems, which are convenient for people at home for virtual try-on of eyeglasses, require the tested subjects to turn their head from left to right so that pictures of their face from different perspectives can be captured for augmented reality. These tablet-based systems are inexpensive and convenient; however, they suffer a number of issues in practice. First, the success rate can be low because most users cannot control their head motion according to how the application software is designed. Second, the relative position between the hand-held device (e.g. tablet, mobile phone) and the head of the tested subject may change during the head rotation, causing failure in capturing qualified pictures of the face at home. Third, the best possible pictures of the tested subjects are rarely captured for virtual try-ons because too much effort is required for the tested subjects during the self-administered operation. Thus, people give up trying as soon as an image is accepted by the software, rather than taking more images that could provide a more accurate fit. All these issues can be addressed with the professional system of the present disclosure because the tested subject by design can remain passive and steady without moving his/her head position or viewing direction.

In some embodiments, the digital camera module 11 of FIG. 1 is further configured for its optical axis to be tilted to non-horizontal so that an oblique view of the face of a tested subject can be captured. The oblique views may be used in the augmented reality of block 17, and can be achieved by using a movable tilt module for tilting the digital camera module around the horizontal axis, where the movable tilt module can include a motor and driving electronics to move the rotation arm by the motor. This feature will allow the best appearance of the tested subject with or without an eyeglass frame to be shown, providing professionally-made selfies of the tested subject. Selfies can be taken at all possible angles at once with the professional system.

In still another aspect, in some embodiments as represented by block 18, the system 10 of FIG. 1 is further configured for providing three-dimensional (3D) measurements of the face for virtually determining the fit of an eyeglass frame to a human face. In one embodiment, the digital camera module 11 is a digital 3D camera module, having at least a plurality of camera lenses, a plurality of image sensors, and camera drivers for acquiring, and optionally saving, images. The digital 3D camera module enables a three-dimensional face map of the tested subject to be generated. The 3D camera module can be moved by the motion control module 12 to capture different perspective views of the human face. The software application 18 in the computer module 13 can generate a 3D face map of the tested subject using the pictures of the tested subject captured by the digital 3D camera. The software application of block 18 can also include instructions to superimpose a 3D virtual eyeglass frame onto the 3D face map of the tested subject. This provides additional information about how well a selected style of eyeglass frame will fit with the face of the tested subject. The fitting of the frame style may include, for example, a tightness of the frame to the face as well as fitting of the nose pad to the facial structures.

The system in the present disclosure allows for selecting eyeglass frames by the tested subject or an operator by checking fitness of eyeglass frames as well as appearance of the eyeglasses using software without the need for putting eyeglass frames on the tested subjects physically. In some embodiments, the computer module 13 can further be configured have an input module 13D for the operator or tested subject to manipulate the appearance of eyeglass frames on a tested subject, and select and order a favored frame. The input module 13D may be, for example, a keyboard, touch screen, joystick, or other input device. The system 10 can be connected to a browser in another computer or an application of a mobile device to allow a user or the tested subject to select different frame styles in a database without the physical presence of the different frame styles. The selection of a frame style can be based on appearances of the tested subject with specific eyeglass frames and/or on a fit of specific eyeglass frames without the frames physically being on the tested subject.

Figure 4:
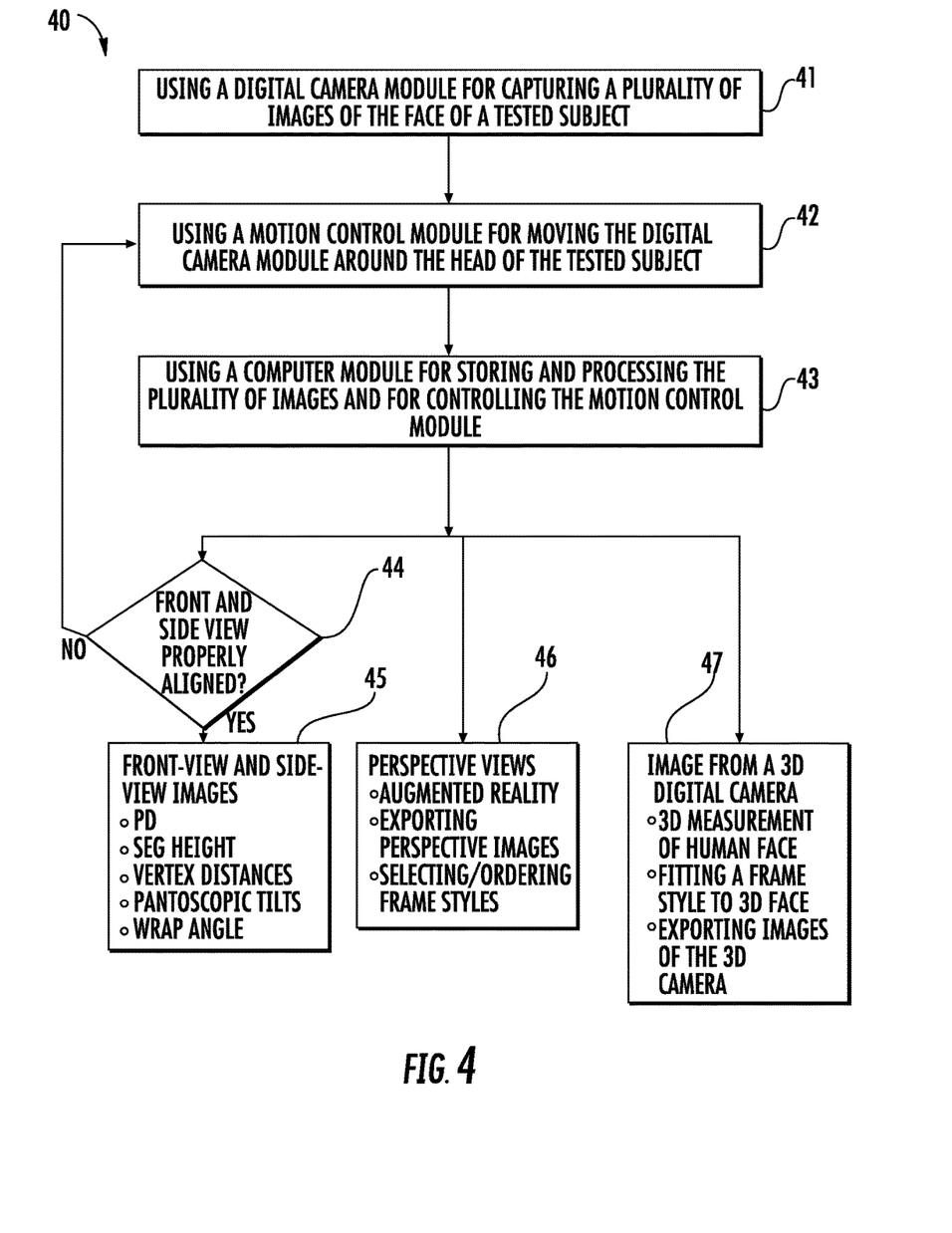
FIG. 4 shows a flow chart of a method for measuring human faces for fitting, selecting, and optimizing eyeglasses in accordance with the present embodiments.

FIG. 4 is an example flow chart 40 of a method for measuring human faces for fitting, selecting and optimizing eyeglass frames according to the present disclosure. The fitting may include, for example, measuring pupillary distances, seg heights, vertex distances and pantoscopic tilts for augmented reality of selecting eyeglass frames, and for fitting eyeglass frames to a human face by capturing 3D measurements of the face.

In step 41, a digital camera module is used for capturing a plurality of images of human face. The a plurality of images have a plurality of perspective views of a tested subject, including a front view and a side view. The tested subject is not required to move their head position or viewing direction during the capturing of images; that is, the tested subject may remain passive and steady. In some embodiments, a target on which an eye of the tested subject can fixate during a measurement is provided, where the target may be, for example, a LED light source or a visible target. In step 42, a motion control module is used to move the digital camera module around the head which allows it to capture images of the human face from various viewing directions. In one embodiment, the moving includes rotating the camera module around the head of the tested subject with an optical axis of the digital camera module pointing to a specified position which serves as a rotation center. This rotation allows the camera module to capture a perfect front view, where the rotating can be controlled by an operator based on the images taken and applying certain criteria to assess the best alignment. The rotation also allows a perfect side view and additional perspective views of the face of the tested subject to be captured. The moving of the camera module in step 42 also includes positioning the digital camera module to adjust the location of the rotation center to accommodate different head positions of the tested subject.

A computer module is connected to the digital camera module as well as the motion control module. In step 43, the computer module is used for processing and storing the plurality of images of the human face from the digital camera module for use in at least one of the steps 45, 46 or 47. If the front view and side view are properly aligned with the face of the tested subject at step 44, then in step 45 the front and side views are used for determining pupillary distance, seg height, vertex distance, and pantoscopic tilt. If the front and side views are not aligned at step 44, the motion control module is used in step 42 to move the digital camera module into proper alignment, and another, corrected plurality of images is taken in step 43. The computer module can also be used to process the perspective views in step 46, such as for providing an augmented reality of different styles of eyeglasses. Step 46 may also include exporting the perspective images, such as to store the images in a database of an external computer server. Additionally, the augmented reality of step 46 may be used for selecting and ordering frame styles. In step 47, the computer module may be used for obtaining 3D measurements of the face for fitting different styles of eyeglass frames to the face of the tested subject. Step 47 may also include exporting images of the 3D camera, such as for storage in a database of the external computer server.

The digital camera module includes a camera lens, an image sensor and control electronics for acquiring images, and the digital camera module is connected to the computer module. The captured images of step 45 include a front view and a side view of a human face with an eyeglass frame having a frame attachment mounted on the eyeglass frame. The frame attachment is decorated with a plurality of marks for determining calibration factors of the digital images, such as converting the image pixels to millimeters (mm/pixels). The calibration involves determining the distance of the calibration marks on the frame attachment in pixels in the digital image, and calculating the calibration factor using the known distance of the marks (e.g., in millimeters) and the determined distance of the same mark in pixels. Using the calibration factor, the front view can be used to determine pupillary distances from determining pupil centers of left and right eyes of the tested subject, and also to determine a segment height by calculating distances from the pupil centers to various edges of the eyeglass frame. The side view of the face with an eyeglass frame and a frame attachment can be used to measure vertex distance by determining a distance from a lens in the eyeglass frame to a cornea of an eye of the tested subject, and to determine pantoscopic tilt as an angle of the eyeglass frame relative to a vertical direction. The vertex distance can be achieved in a similar manner as described above by finding the distance of the feature in pixels, calculating a calibration factor from the known distances in the calibration marks on the frame attachment, and determining the vertex distance in mm. Because the pantoscopic tilt in the real space is the same in the image space, the pantascopic tilt can be directly measured in the side-view images.

The captured images of step 46 include a large number of perspective views of the human face, such as one image taken in every 20 rotation degrees, without an eyeglass frame, from which an augmented reality of different styles of eyeglass frames can be presented. The plurality of perspective views comprises a plurality of viewing angles from a left side view to a right side view of the face. The augmented reality is provided by using a software module to retrieve images of different styles of eyeglass frames from an eyeglass frame database, and to superimpose the images of the different styles of eyeglass frames onto the plurality of perspective views of the face for displaying an appearance of the tested subject with the different styles of eyeglass frames. The eyeglass frame database may be, for example, a database supplied from an eyeglass frame vendor, or a customized database for the operator of the system. The augmented reality for virtual try-on with the professional system in the present disclosure can overcome problems of conventional tablet-based systems by enabling 1) increased success rate and reduced measurement times because the images are taken with a camera rotated around the head by a professional instead of uncontrolled operation by the user, and 2) more accurate fitting to the frames because physical parameters of human face can be precisely measured with the professional system that is properly aligned with the patient's face. In some embodiments, the plurality of digital images captured by the digital camera module are exported to an external computer server. The external computer server comprises an external computer software module that includes instructions to retrieve the images of different styles of eyeglass frames from a database, and to superimpose the images of different styles of eyeglass frames onto the plurality of perspective views of the face.

In another embodiment described in step 47 of FIG. 4, the digital camera module is a digital 3D camera module, having at least a plurality of camera lenses, a plurality of image sensors, and camera drivers for acquiring images. The 3D camera module can be moved by the motion control module as controlled by the computer module, for capturing the perspective view images of the human face. A software application in the computer module can generate a 3D face map of the tested subject using the plurality of images captured by the digital 3D camera. The software application can be further include instructions for superimposing a 3D virtual eyeglass frame onto the 3D face map of the tested subject. This provides additional information about how well a selected eyeglass frame will fit with the face of a tested subject. Unlike the traditional imaging (2D) systems, the 3D system in the present disclosure allows for evaluation of fitting factors such as tightness of the eyeglass frame to the face as well as fitness of the nose pad to the facial structures. The fitting of eyeglasses, using images captured by the 3D camera, uses the 3D measurements to check fitness of a frame of the different styles of eyeglass frames, without the need for the frame to be placed on the tested subject physically. The method may also include having the tested subject or an operator select a desired eyeglass frame from the different styles of eyeglass frames.

Figure 5:
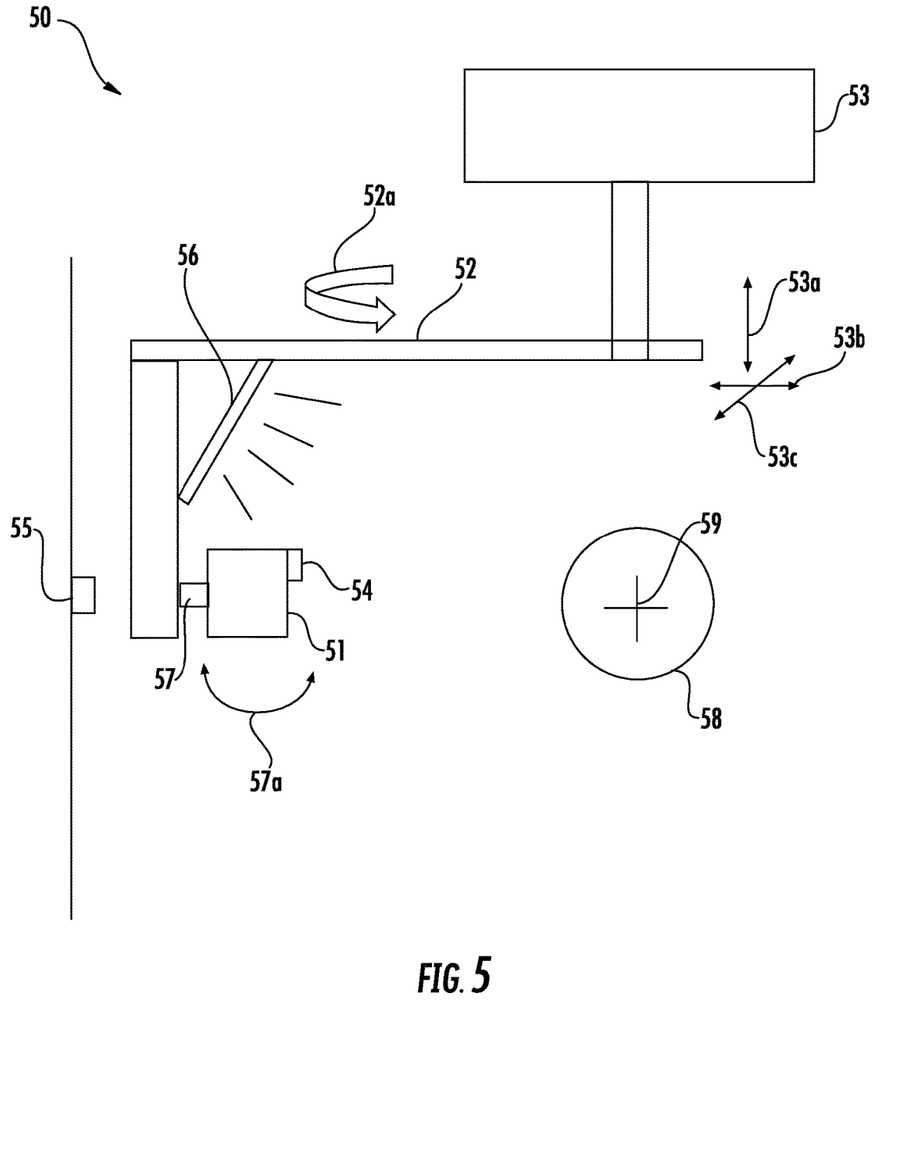
FIG. 5 is a side view of an example system in accordance with the present embodiments.

FIG. 5 is a simplified illustration of a side view of a system 50 for measuring human faces for eyeglass measurement according to the present embodiments. There are a number of ways for moving the camera module 51 with its optical axis pointing to a rotation center 59 and for moving the camera module up-and-down as well as left-and-right in order to capture images of the face of head 58. In one embodiment, the system has a translation module 53 for linearly moving the digital camera module 51 up-and-down, left-and-right and forward-and-backward as indicated by arrows 53a, 53b and 53c, respectively. The system 50 also has a rotation arm module 52 for rotating the digital camera module 51 around the head 58 of a tested subject, as indicated by arrow 52a. Thus, the rotation arm module 52 and translation module 53 are able to move the digital camera module 51 in three dimensions. The translation module 53 and rotation arm module 52 may be actuated using, for example, a motorized system, pneumatics, hydraulics, or other mechanical movement methods. In one embodiment, a motorized rotation arm module 52 includes a rotation arm, a motor, and driving electronics to move the rotation arm by the motor. In some embodiments, a motion control module is configured like a robotic arm for rotating and translating the camera module 51, such that the rotation and translation are combined in one motion control module that encompasses both the rotation module 52 and translation module 53 that are illustrated in FIG. 5. In one embodiment, the system for measuring human face for eyeglasses further comprises a tilt module 57, which can make the optical axis of the camera module 51 to be at an angle to the horizontal axis as indicated by arrow 57a. This allows the camera module 51 to take pictures of the face of the tested subject according to individual preferences in his/her selfies. The tilt module 57 may comprise a motor and driving electronics that move the tilt arm by the motor, to tilt the digital camera module around a horizontal axis.

Additionally, the system 50 can be further configured to have a light source 56 for illumination of the digital camera modules, and to have at least one target 54 or 55 for the tested eye to fixate at during a measurement. In one embodiment, the target 54 is coupled to the moving rotation arm 52, such as being placed on the camera module 51. In another embodiment a target 55 is detached from the rotation arm 52, e.g., mounted on wall of the examining room.

While the specification has been described in detail with respect to specific embodiments of the invention, it will be appreciated that those skilled in the art, upon attaining an understanding of the foregoing, may readily conceive of alterations to, variations of, and equivalents to these embodiments. These and other modifications and variations to the present invention may be practiced by those skilled in the art, without departing from the scope of the present invention, which is more particularly set forth in the appended claims. Furthermore, those skilled in the art will appreciate that the foregoing description is by way of example only, and is not intended to limit the invention.

What is claimed is:

1. A system for measuring human faces for eyeglasses, comprising:
   a digital camera module positioned to capture a plurality of digital images of a face of a tested subject, wherein the plurality of digital images comprise a plurality of perspective views including a front view and a side view, and wherein the digital camera module includes a camera lens, an image sensor, and control electronics capable of acquiring the plurality of digital images;
   a motion control module that i) rotates the digital camera module around a head of the tested subject with an optical axis of the digital camera module pointing at a specified position in space, wherein the rotating corrects any orientation error in capturing the plurality of perspective views, and ii) positions the digital camera module to adjust the specified position for accommodating different head positions of the tested subject; and
   a computer module that processes and stores the plurality of digital images of the face of the tested subject at the plurality of perspective views, the computer module including a display, a storage unit, and a processor, wherein the computer module is connected to the digital camera module and the motion control module; and
   wherein the processor of the computer module stores instructions to use the plurality of digital images to fit an eyeglass frame to the tested subject or to acquire data for fitting prescription lenses into the eyeglass frame.

2. The system of claim 1 wherein the motion control module comprises:

a motorized rotation arm that rotates the digital camera module around the specified position; and
a translation module that linearly moves the digital camera module.

3. The system of claim 1 further comprising a frame attachment that is decorated with a plurality of marks for determining a calibration factor of the plurality of digital images, the frame attachment being mountable to the eyeglass frame, the eyeglass frame being worn by the tested subject during the capturing of the plurality of digital images.

4. The system of claim 3 wherein the computer module processes the front view to i) identify pupil centers of left and right eyes of the tested subject, and ii) calculate distances from the pupil centers to edges of the eyeglass frame in different directions based on the calibration factor.

5. The system of claim 3 wherein the computer module determines pupillary distances of left and right eyes of the tested subject.

6. The system of claim 3 wherein the computer module processes the side view to i) determine a distance from the prescription lens in the eyeglass frame to a cornea of an eye of the tested subject, and ii) determine an angle of the eyeglass frame relative to a vertical direction.

7. The system of claim 1 wherein the plurality of perspective views of the face includes images of the face at plurality of viewing angles from a left side-view to a right side-view of the face, the plurality of perspective views being stored in the computer module.

8. The system of claim 7 wherein:
the computer module further comprises a software module that includes instructions to retrieve images of different styles of eyeglass frames, and to superimpose the images of the different styles of eyeglass frames onto the plurality of perspective views of the face; and
the computer module displays the superimposed images of the tested subject with the different styles of eyeglass frames.

9. The system of claim 7 wherein:
the computer module exports the plurality of digital images captured by the digital camera module to an external computer server; and
the external computer server comprises an external computer software module that includes instructions to retrieve the images of different styles of eyeglass frames from a database, and to superimpose the images of different styles of eyeglass frames onto the plurality of perspective views of the face.

10. The system of claim 1 wherein the computer module further comprises a software module, the software module including instructions to allow a user or the tested subject to select different frame styles from a database.

11. The system of claim 10 wherein the computer module is connected to a browser in another computer or an application of a mobile device to allow the user or the tested subject to select the different frame styles in the database, without a physical presence of the different frame styles, based on a) appearances of the tested subject with specific eyeglass frames of the database or b) a fit of the specific eyeglass frames on the tested subject.

12. The system of claim 1 further comprising a tilt module that tilts the digital camera module around a horizontal axis, wherein the tilt module comprises a motor and driving electronics that move the tilt module by the motor.

13. The system of claim 1 wherein the digital camera module is a 3D camera comprising a plurality of the camera lenses and a plurality of the image sensors, enabling a three-dimensional (3D) face map of the tested subject to be generated.

14. The system of claim 13 wherein the computer module stores instructions to superimpose a 3D virtual eyeglass frame onto the 3D face map of the tested subject.

15. The system of claim 1 further comprising a target on which an eye of the tested subject can fixate during a measurement.

16. A method of measuring human faces for eyeglasses, the method comprising:
capturing, using a digital camera module, a plurality of digital images comprising a plurality of perspective views of a face of a tested subject, including a front view and a side view, wherein the tested subject is not required to move a head position or a viewing direction of the tested subject during the capturing of the plurality of digital images;
using a motion control module to move the digital camera module, the moving comprising: i) rotating the digital camera module around a head of the tested subject with an optical axis of the digital camera module pointing at a rotation center, wherein the rotating orients the digital camera module for capturing the front view and the side view, and ii) positioning the digital camera module to adjust the rotation center for accommodating different head positions of the tested subject; and
processing and storing, using a computer module, the plurality of digital images, the processing comprising: i) determining a pupillary distance, a segment height, a vertex distance, or a pantoscopic tilt, ii) providing an augmented reality of different styles of eyeglass frames, or iii) obtaining 3D measurements of the face for fitting the different styles of eyeglass frames to the face of the tested subject;
wherein the computer module is connected to the digital camera module and the motion control module.

17. The method of claim 16 wherein during the capturing of the plurality of digital images, the tested subject is required to wear a frame attachment mounted on an eyeglass frame, the frame attachment being decorated with a plurality of marks for determining a calibration factor of the plurality of digital images.

18. The method of claim 17 wherein the processing comprises processing the front view to determine the pupillary distance and the segment height by a) determining pupil centers of left and right eyes of the tested subject, and b) calculating distances from the pupil centers to edges of the eyeglass frame in different directions based on the calibration factor.

19. The method of claim 18 wherein the processing comprises processing the side view to a) determine the vertex distance as a distance from a lens in the eyeglass frame to a cornea of an eye of the tested subject, and b) determine the pantoscopic tilt as an angle of the eyeglass frame relative to a vertical direction.

20. The method of claim 16 wherein:
the providing of the augmented reality comprises capturing the plurality of perspective views without the tested subject wearing an eyeglass frame;
the plurality of perspective views comprises a plurality of viewing angles from a left side-view to a right side-view of the face; and
the augmented reality is provided by using a software module to retrieve images of the different styles of eyeglass frames from an eyeglass frame database and superimpose the images of the different styles of eyeglass frames onto the plurality of perspective views of the face for displaying an appearance of the tested subject with the different styles of eyeglass frames.

21. The method of claim 20 further comprising:
exporting to an external computer server the plurality of perspective views of the tested subject without wearing an eyeglass frame;
saving the plurality of perspective views in a database of the external computer server;
retrieving, using the external computer server, the images of the different styles of eyeglass frames from an eyeglass frame database; and
superimposing, using the computer module, the images of different styles of eyeglass frames onto the plurality of perspective views of the face.

22. The method of claim 16 wherein the motion control module further comprises a tilt module that tilts the digital camera module around a horizontal axis, wherein the tilt module comprises a motor and driving electronics that move the tilt module by the motor.

23. The method of claim 16 wherein:
the digital camera module is a 3D camera includes a plurality of camera lenses and a plurality of image sensors; and
wherein the method further comprises generating a 3D face map of the tested subject using the plurality of digital images.

24. The method of claim 23 further comprising superimposing a 3D virtual eyeglass frame onto the 3D face map of the tested subject.

25. The method of claim 16 further comprising:
using the 3D measurements to check fitness of a frame of the different styles of eyeglass frames, without a need of the frame of the different styles of eyeglass frames to be physically present on the tested subject; and
having the tested subject or an operator select a desired eyeglass frame from the different styles of eyeglass frames.

26. The method of claim 25 wherein the computer module is connected to a browser in another computer or to an application of a mobile device to allow a user or the tested subject to select a desired frame from the different styles of eyeglass frames, stored in an eyeglass frame database, without the physical presence of the different styles of eyeglass frames, based on a) an appearance of the tested subject with the desired frame using the augmented reality, or b) the fitting of the desired frame to the face of the tested subject.

27. The method of claim 16 further comprising providing a target on which an eye of the tested subject can fixate during a measurement.

* * * * *